United States Patent [19]

Krapcho

[11] 4,252,943
[45] Feb. 24, 1981

[54] CARBAMATE DERIVATIVES OF MERCAPTOACYL HYDROXY PROLINES

[75] Inventor: John Krapcho, Somerset, N.J.

[73] Assignee: E. R. Squibb & Sons, Inc., Princeton, N.J.

[21] Appl. No.: 113,152

[22] Filed: Jan. 18, 1980

Related U.S. Application Data

[60] Division of Ser. No. 66,119, Aug. 13, 1979, which is a continuation-in-part of Ser. No. 3,178, Jan. 15, 1979, abandoned.

[51] Int. Cl.$^3$ ............................................. C07D 207/16
[52] U.S. Cl. ................................ 544/141; 260/326.2; 260/326.25; 260/326.43; 260/326.46; 546/208; 424/248.5; 424/267; 424/274
[58] Field of Search ...................... 260/326.46, 326.25, 260/326.2; 546/208; 544/141

[56] References Cited

U.S. PATENT DOCUMENTS

| | | | |
|---|---|---|---|
| 3,932,638 | 1/1976 | Coirre et al. | 260/326.2 |
| 4,046,889 | 9/1977 | Ondetti et al. | 260/326.2 |
| 4,105,776 | 8/1978 | Ondetti et al. | 260/326.2 |

OTHER PUBLICATIONS

Coirre et al., Chem. Abs. vol. 78:P124436b (1973).
Coirre et al., Chem. Abs. vol. 77:P127056t (1972).
Coirre et al., Chem. Abs. vol. 84:P140736d (1976).

Primary Examiner—Mary C. Lee
Attorney, Agent, or Firm—Lawrence S. Levinson; Burton Rodney

[57] ABSTRACT

New carbamate derivatives of mercaptoacyl hydroxy prolines which have the general formula

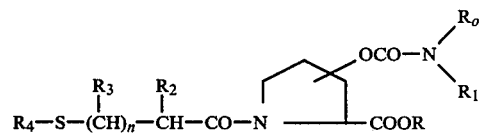

are useful as hypotensive agents.

3 Claims, No Drawings

CARBAMATE DERIVATIVES OF MERCAPTOACYL HYDROXY PROLINES

REFERENCE TO OTHER APPLICATIONS

This application is a division of application Ser. No. 066,119, filed Aug. 13, 1979, which is a continuation-in-part of application Ser. No. 003,178, filed Jan. 15, 1979, now abandoned.

SUMMARY OF THE INVENTION

This invention relates to new carbamate derivatives of mercaptoacyl hydroxy prolines which have the formula

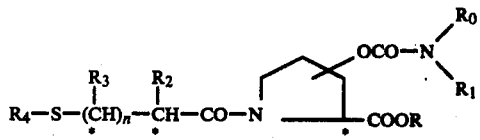

wherein

R, $R_2$ and $R_3$ each is hydrogen or lower alkyl;

$R_0$ and $R_1$ each is hydrogen, lower alkyl, cyclo-lower alkyl, allyl, propargyl, phenyl or substituted phenyl; or $R_0$ and $R_1$ can join with the nitrogen to form a 5- or 6-membered heterocyclic;

$R_4$ is hydrogen or a hydrolyzable organic protecting group of the formula $R_5$—CO— or

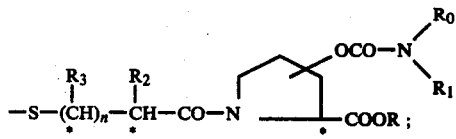

$R_5$ is lower alkyl, phenyl, substituted phenyl, phenyl-lower alkyl, substituted phenyl-lower alkyl, cycloalkyl, thienyl, or furyl;

n is 0, 1 or 2;

and salts thereof, as well as novel intermediates therefor.

The asterisks indicate centers of asymmetry. The carbon in the acyclic side chain is asymmetric when $R_2$ and/or $R_3$ is other than hydrogen. Each of the centers of asymmetry provide D and L forms which can be separated by conventional methods as described below. The carbamate group

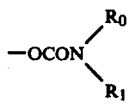

also gives rise to cis-trans isomerism.

BACKGROUND OF THE INVENTION

U.S. Pat. No. 4,105,776, issued Aug. 8, 1978 to Miguel Angel Ondetti and David W. Cushman, and its parent U.S. Pat. No. 4,046,889, issued Sept. 6, 1977, disclose certain mercaptoacyl derivatives of the naturally occurring amino acids proline and hydroxyproline which are angiotensin converting enzyme inhibitors and can be used for the reduction of blood pressure. It has now been found that certain synthetic hydroxyproline derivatives, wherein the pyrrolidine ring of proline bears a carbamate group, also provide new chemical compounds which have utility as hypotensive agents.

DETAILED DESCRIPTION OF THE INVENTION

This invention relates to new compounds which have the formula

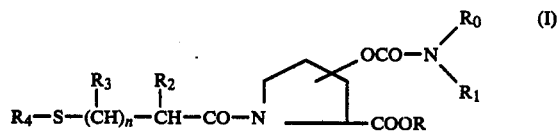

and to salts thereof, to compositions containing such compounds and to the method for using such compounds as anti-hypertensive agents. The symbols have the meanings defined above.

The lower alkyl groups represented by any of the variables include straight and branched chain hydrocarbon radicals having up to seven carbons, for example, methyl, ethyl, propyl, isopropyl, butyl, isobutyl, t-butyl, pentyl, isopentyl and the like. The lower alkyl groups having up to four carbons and especially the $C_1$ and $C_2$ members are preferred.

The cyclo-lower alkyl groups are the alicyclic groups having up to seven carbons, i.e., cyclopropyl, cyclobutyl, cyclopentyl, cyclohexyl and cycloheptyl. Cyclopentyl and cyclohexyl are preferred.

The substituted phenyl groups include monosubstituted phenyl rings wherein the phenyl substituent is halogen, lower alkyl, lower alkoxy, lower alkylthio or trifluoromethyl. The lower alkoxy and lower alkylmercapto groups include lower alkyl groups of the type described above. Exemplary are methoxy, ethoxy, propoxy, isopropoxy, butoxy, t-butoxy, methylthio, ethylthio, propylthio, isopropylthio and the like. The $C_1$-$C_4$ and $C_1$-$C_2$ preferences described above also apply. The halogens are the four common halogens, preferably chorine and bromine, providing such radicals as o-, m- and p-chlorophenyl, o-, m- and p-bromophenyl and the like. The phenyl and substituted phenyl can also be described as

wherein $R_6$ is hydrogen, halogen, lower alkyl, lower alkoxy, lower alkylthio or trifluoromethyl.

The phenyl-lower alkyl groups include lower alkyl groups of the type described above attached to the phenyl ring. Phenylmethyl and phenylethyl are the preferred phenyl-lower alkyl groups, especially phenylmethyl.

The preferred groups of the formula $R_5$—CO— are those wherein $R_5$ is lower alkyl, phenyl, or phenyl-lower alkyl.

The lower alkanoyl groups represented by $R_5$—CO— are those having the acyl radicals of the lower ($C_2$-$C_7$) fatty acids, for example, acetyl, propionyl, butyryl, isobutyryl and the like. Those lower alkanoyl groups having up to four carbons, and especially acetyl, are preferred. The same preferences apply to the phenyl-lower alkanoyl groups when $R_5$ in the group $R_5$—

CO— is phenyl-lower alkyl. Benzoyl is especially preferred.

The carbamate group on the pyrrolidine ring can be acyclic including, for example, the radicals carbamoyl, lower alkylcarbamoyl like methylcarbamoyl, ethylcarbamoyl, propylcarbamoyl, isopropylcarbamoyl, di(-lower alkyl)carbamoyl like dimethylcarbamoyl, diethylcarbamoyl, propargylcarbamoyl, or allylcarbamoyl. It also includes cycloalkylcarbamoyl groups like cyclopentylcarbamoyl, dicyclopentylcarbamoyl, cyclohexylcarbamoyl, dicyclohexylcarbamoyl and the like. In addition it includes phenyl- and substituted phenylcarbamoyl groups like phenylcarbamoyl, 4-chlorophenylcarbamoyl, 3-ethylphenylcarbamoyl, 4-methoxyphenylcarbamoyl, 4-(trifluoromethyl)phenylcarbamoyl and the like. Preferably only one of $R_0$ and $R_1$ is a cycloalkyl, phenyl or substituted phenyl radical.

The

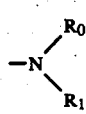

can also form a 5-membered or 6-membered heterocyclic of the group pyrrolidine, piperidine or morpholine.

Preferably only one of $R_0$ and $R_1$ is other than hydrogen except when both $R_0$ and $R_1$ are lower alkyl.

Preferred compounds of formula I are those wherein R is hydrogen or lower alkyl; $R_0$ and $R_1$ each is independently $C_1$–$C_4$-lower alkyl; $R_2$ and $R_3$ each is hydrogen or $C_1$–$C_4$-lower alkyl; $R_4$ is hydrogen, lower alkanoyl, or benzoyl; and n is 0 or 1. The carbamate group is in the 3- or 4-position of the pyrrolidine ring, preferably the 4-position.

Especially preferred are compounds of formula I wherein R is hydrogen; $R_0$ and $R_1$ each is $C_1$–$C_4$ lower alkyl, most especially $C_1$–$C_3$-lower alkyl; $R_2$ is methyl; $R_3$ is hydrogen; $R_4$ is hydrogen; n is 1; and the carbamate group is in the 4-position.

The preferred method of synthesizing compounds of formula I utilizes as starting material a hydroxyproline of the formula

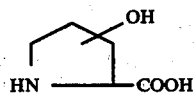

The nitrogen is first protected, e.g., with a nitrogen protecting group of the type commonly used in peptide synthesis like carbobenzoxy, p-toluenesulfonyl, acetyl or the like to obtain a protected compound such as

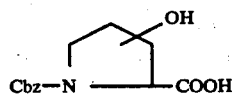

wherein CBz is the carbobenzoxy protecting group.

The protected comound III is then esterified, for example, by reaction with a diazoalkane, such as diazomethane to form an ester of the structure

wherein R is lower alkyl like methyl or isobutyl, preferably methyl.

The carbamate group

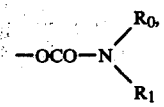

wherein $R_0$ is hydrogen and $R_1$ is other than hydrogen, can then be introduced by reacting the compound of formula IV with an isocyanate ($R_1$—NCO) in an inert organic solvent like benzene, and the like to obtain the next intermediate having the formula

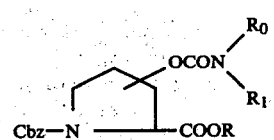

In the preparation of the cis isomer, the above reaction is carried out in the presence of a catalytic amount of a base, such as pyridine or triethylamine.

Alternatively, compounds of formula V may be prepared by reacting the protected compound IV with phosgene to form an intermediate of formula VI

(which is not necessarily isolated), which is then reacted with the appropriate amine

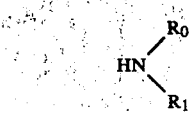

or $NH_3$ (where both $R_0$ and $R_1$ are to be hydrogen) to form the formula V compound.

When $R_0$ and $R_1$ (in formula V) are both to be other than hydrogen or together complete a heterocyclic, then the protected compound of formula IV is made to react with the carbamoyl halide

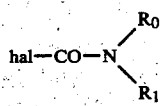

wherein hal is halogen, preferably chlorine.

Alkaline hydrolysis of the compound of formula V with a base like sodium hydroxide, barium hydroxide, potassium hydroxide or the like yields the acid having the formula

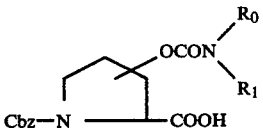

The compound of formula VIII can then be deprotected, e.g., by the conventional procedure of hydrogenation in the presence of palladium-carbon to obtain the compound having the formula

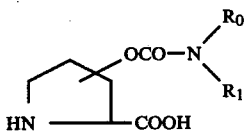

The next stage of the synthesis entails coupling the proline derivative IX with an acyl halide having the formula

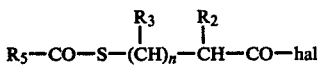

wherein hal represents halogen preferably chlorine, yielding a product of the formula

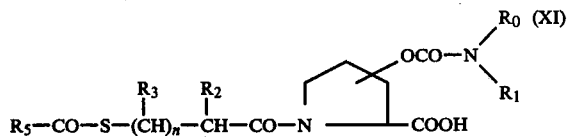

The proline derivative XI is preferably isolated and purified by crystallization, e.g., by forming a salt like the dicyclohexylamine salt and then converting the salt to the free acid form by treatment with an aqueous solution of an acid, such as potassium acid sulfate.

The product of formula XI bearing the acyl group $R_5$—CO can be converted, if desired, to the product of formula I wherein $R_4$ is hydrogen by hydrolysis with ammonia, sodium hydroxide or the like.

Esters of formula I wherein R is lower alkyl can be obtained by conventional esterification procedures, e.g., by esterification with a diazoalkane like diazomethane, 1-alkyl-3-p-tolyltriazene, like 1-n-butyl-3-p-tolyltriazene, or the like, preferably after the completion of the sequence of reactions described above. However, earlier esterification and omission of the alkaline hydrolysis can also be practiced.

The compounds of formula I wherein $R_4$ forms the symmetrical bis compound are obtained by directly oxidizing with iodine a product of formula I wherein $R_4$ is hydrogen.

Reference is also made to the following publications for additional illustrative information with respect to the production of starting materials and intermediates: U.S. Pat. Nos. 4,046,889 and 4,105,776; J. Chem. Soc., 1945, 429–432; J. Amer. Chem. Soc. 79, 185–192 (1957); J. Amer. Soc. 85, 3863–3865 (1963). The procedures illustrated therein can be utilized as general methods for the synthesis and stereoconversion of compounds utilizable in the invention of this application.

Additional experimental details are found in the examples which are preferred embodiments and also serve as models for the preparation of other members of the group.

As indicated above, the compounds of this invention have several centers of asymmetry. These compounds accordingly exist in stereoisomeric forms or in racemic mixtures thereof. The various stereoisomeric forms and mixtures thereof are all within the scope of this invention. The above described methods of synthesis can utilize the racemate or one of the enantiomers as starting material. When a mixture of stereoisomers is obtained as the product, the stereoisomeric forms can be separated, if desired, by conventional chromatographic or fractional crystallization methods or by conversion to a salt with an optically active base, followed by fractional crystallization or similar known methods. In general, those compounds are preferred wherein the proline moiety is in the L-configuration, the carbamate group is cis and the acyl side chain has the D-configuration.

The compounds of this invention form basic salts with a variety of inorganic or organic bases. The salt forming ion derived from such bases can be metal ions, e.g., aluminum, alkali metal ions, such as sodium or potassium, alkaline earth metal ions such as calcium or magnesim, or an amine salt ion, of which a number are known for this purpose, for example, aralkylamines like, dibenzylamine, N.N-dibenzylethylenediamine, lower alkylamines like methylamine, triethylamine, t-butylamine, procaine, lower alkylpiperidines like N-ethylpiperidine, cycloalkylamines like cyclohexylamine, dicyclohexylamine, 1-adamantaneamine, benzathine, or salts derived from amino acids like arginine, lysine or the like. The physiologically aceptable salts like the sodium or potassium salts can be used medicinally as described below and are preferred. These and other salts which are not necessarily physiologically acceptable are useful in isolating or purifying a product acceptable for the purposes described below as well as purifying or isolating intermediates, as illustrated in the examples. The salts are produced by reacting the acid form of the compound with an equivalent of the base supplying the desired basic ion in a medium in which the salt precipitates or in aqueous medium and then lyophilizing. The free acid form can be obtained from the salt by conventional neutralization techniques, e.g., with potassium bisulfate, hydrochoric acid, etc.

The compounds of this invention inhibit the conversion of the decapeptide angiotensin I to angiotensin II by angiotensin converting enzyme and therefore are useful in reducing or relieving hypertension in various mammalian species, e.g., cats, dogs, mice, rats, etc., having elevated blood pressure. Thus by administration of a hypotensively effective amount of a composition containing one or a combination of compounds of formula I or physiologically acceptable salt thereof, hypertension in the species of mammal suffering therefrom is reduced or alleviated.

A single dose, or preferably two or four divided daily doses, provided in a basis of about 0.1 to 100 mg. per kilogram per day, preferably about 1 to 15 mg. per kilogram per day, is appropriate to reduce blood pressure as indicated in the animal model experiments described by S. L. Engel, T. R. Schaeffer, M. H. Waugh and B. Rubin, Proc. Soc. Exp. Biol. Med. 143, 483 (1973). The substance is preferably administered orally, but parenteral routes such as subcutaneously, intramuscularly, intravenously or intraperitoneally can also be employed.

The compounds of this invention can also be formulated in combination with a diuretic for the treatment of hypertension. A combination product comprising a compound of this invention and a diuretic can be administered in an effective amount which comprises (for a 70 kg. mammal) a total daily dosage of about 30 to 600 mg., preferably about 30 to 300 mg., of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorthiazide, hydrochlorthiazide, flumethiazide, hydroglumethiazide, bendroflumethiazide, methylchlorthiazide, trichloromethiazide, polythiazide or benzthiazide, as well as ethacrynic acid, ticrynafen, chlorthalidone, furosemide, bumetanide, triamterene, amiloride and spironolactone, and salts of such compounds.

The compounds of this invention can be utilized to achieve the reduction of blood pressure by formulating in compositions such as tablets, capsules or elixirs for oral administration or in sterile solutions or suspensions for parenteral administration. About 10 to 500 mg. of a compound or mixture of compounds of formula I or physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that suitable dosage in the range indicated is obtained.

Illustrative of the adjuvants which may be incorporated in tablets, capsules and the like are the following: a binder such as gum tragacanth, acacia, corn starch or gelatin; an excipient such as dicalcium phosphate or microcrystalline cellulose; a disintegrating agent such as corn starch, potato starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc. or synthetic like ethyl oleate.

The following examples are illustrative of the invention and constitute preferred embodiments. They also serve as models for the preparation of other members of the group which can be produced by replacement of the given reactants with suitably substituted analogs. All temperatures are in degrees Celsius.

EXAMPLE 1 trans-1-[D-(3-Acetylthio)-2-methyl-1-oxopropyl]-4-[[(methylamino)carbonyl]oxy]-L-proline (a) N-Carbobenzyloxy-trans-4-hydroxy-L-proline 26.5 g. (0.20 mole) of trans-4-hydroxy-L-proline and 32.8 ml. (0.23 mole) of benzyl chloroformate are reacted in 200 ml. of water and 100 ml. of acetone in the presence of 20 g. (0.20 mole) of potassium bicarbonate and 69.2 g. (0.50 mole) of potassium carbonate and worked up with 90 ml. of concentrated hydrochloric acid as described in Can. J. Biochem. & Physiol. 37, 584 (1959). The product is reacted with cyclohexylamine to form the cyclohexylamine salt, yield 69 g., m.p. 193°–195°. The salt (34 g.) is neutralized with N hydrochloric acid to obtain 27 g. of the free acid as a colorless glass $[\alpha]_D^{26} -70°$ (c,1% in chloroform).

(b) N-Carbobenzyloxy-trans-4-hydroxy-L-proline, methyl ester 12.4 g. (0.047 mole) of N-carbobenzyloxy-trans-4-hydroxy-L-proline is esterified with diazomethane in dioxane-ether as described in J.A.C.S. 79, 191 (1957). To avoid freezing of the dioxane the addition of the diazomethane is begun at 10° and completed at 0°–2°. The yield of N-carbobenzyloxy-trans-4-hydroxy-L-proline, methyl ester as a nearly colorless viscous oil is 14.6 g. (100%). $[\alpha]_D^{26} -62°$ (c, 1% in chloroform).

(c) trans-N-Carbobenzyloxy-4-[[(methylamino)carbonyl]oxyl]-L-proline, methyl ester To a stirred solution of 6.0 g (0.021 mole) of N-carbobenzyloxy-trans-4-hydroxy-L-proline, methyl ester (J.A.C.S. 79 supra) in 120 ml. of benzene is added 6 ml. (0.10 mole) of methylisocyanate and the reaction mixture kept overnight at room temperature. After refluxing for one hour, the solvent is removed on a rotary evaporator, finally at 0.2 mm and 50°. The viscous residue is taken up in 150 ml. of ether, washed with water (3×50 ml.), dried (MgSO4), and the ether is evaporated to yield 6.5 g. (90%) of syrupy product, trans-N-carbobenzyloxy-4-[[(methylamino)carbonyl]oxy]-L-proline, methyl ester.

(d) trans-N-Carbobenzyloxy-4-[[(methylamino)carbonyl]oxy]-L-proline

The crude ester from part c (7.6 g., 0.023 mole) is dissolved in 60 ml. of methanol, treated dropwise at −1° to 4° with 14 ml. (0.028 mole) of 2 N sodium hydroxide, kept at 0° for one hour, and at room temperature overnight. After removing about ½ of the solvent on a rotary evaporator, the solution is diluted with 160 ml. of water, washed with ether (wash discarded), acidified, while cooling, with 5.5 ml. of 1:1 hydrochloric acid to pH 2, and extracted with ethyl acetate (4×75 ml.). The combined extracts are washed with 50 ml. of saturated sodium chloride, dried (MgSO4) and the solvent evaporated to give 7.2 g. of a very viscous syrup. The syrup is dissolved in 30 ml. of ethanol, treated with 2.3 g. of cyclohexylamine in 5 ml. of ethanol and diluted to 600 ml. with ether. On seeding and rubbing, the crystalline cyclohexylamine salt separates; weight after cooling overnight, 8.5 g.; m.p. 172°–174°. $[\alpha]_D^{25} -20°$ (c, 1% in ethanol). Following crystallization from 25 ml. of isopropanol, the colorless solid trans-N-carbobenzyloxy-4-[[(methylamino)carbonyl]oxy]-L-proline cyclohexylamine salt weighs 7.8 g., m.p. 174°–176°. $[\alpha]_D^{25} -18°$ (c, 1% in ethanol).

The cyclohexylamine salt is suspended in 60 ml. of ethyl acetate, stirred, and treated with 40 ml. of N hydrochloric acid. When two clear layers are obtained they are separated, the aqueous phase is extracted with additional ethyl acetate (3×60 ml.), the combined organic layers are dried (MgSO$_4$), and the solvent evaporated. The yield of glass-like free acid is 5.5 g. (81%).

(e) trans-4-[[(Methylamino)carbonyl]oxy]-L-proline

A solution of 2.7 g. (0.0084 mole) of trans-N-carbobenzyloxy-4-[[(methylamino)carbonyl]oxy]-L-proline in 100 ml. of methanol-water (2:1) is treated with 1 g. of 5% palladium-carbon and 45 lb. of hydrogen and shaken on a Parr hydrogenator for 6 hours. The catalyst is filtered off under nitrogen, washed with methanol and the combined filtrates are evaporated, finally at 0.1–0.2 mm, to give 1.5 g. (96%) of a residue which gradually crystallizes to give trans-4-[[(methylamino)carbonyl]oxy]-L-proline as a greyish solid; m.p. 213°–215° (dec.), preceded by gradual darkening and sintering. [α]$_D^{26}$ −12° (c, 0.25% in 1:3 ethanol-methanol).

(f) trans-1-[D-(3-Acetylthio)-2-methyl-1-oxopropyl]-4-[[(methylamino)carbonyl]oxy]-L-proline A stirred solution of 2.9 g. (0.0154 mole) of trans-4-[[(methylamino)carbonyl]oxy]-L-proline in 45 ml. of water is cooled to 5° and treated portionwise with solid sodium carbonate to pH 8.5; (approx. 0.4 g. required). Then while continuing stirring and cooling, a solution of 3.1 g. (0.017 mole) of D-3-acetylthio-2-methylpropanoyl chloride in 4 ml. of ether is added portionwise by means of a pipette while maintaining the pH at 7.0–8.0 by dropwise addition of 25% (w/v) sodium carbonate. After about 10 minutes, the pH stabilizes at 8.1–8.3 (about 14 ml. of the sodium carbonate solution has been added). After continued stirring and cooling for a total of 1.25 hours, the solution is washed with ethyl acetate (50 ml.), layered over with 50 ml. of ethyl acetate, stirred, cooled, acidified carefully with 1:1 hydrochloric acid to pH 2.0, saturated with sodium chloride and the alyers are separated. The aqueous phase is extracted with additional ethyl acetate (3×50 ml.), the combined organic layers are dried (MgSO$_4$) and the solvent evaporated, finally at 0.2 mm., to give 5.3 g. of a glass-like residue. The latter is dissolved in 40 ml. of ethyl acetate and treated with a solution of 2.8 g. of dicyclohexylamine in 15 ml. of ethyl acetate. On seeding and rubbing, the crystalline trans-1-[D-(3-acetylthio)-2-methyl-1-oxopropyl]-4-[[(methylamino)carbonyl]oxy]-L-proline dicyclohexylamine salt separates, weight after cooling overnight 5.8 g. (colorless); m.p. 187°–189° (s. 183°) [α]$_D^{26}$ −64° (c, 1% in MeOH). Following recrystallization from 15 ml. of methanol—100 ml. of ether, the colorless solid weighs 4.5 g., m.p. 190°–192° [α]$_D^{25}$ −67° (c, 1% in MeOH).

The dicyclohexylamine salt is converted to the free acid by suspending in 50 ml. of ethyl acetate, cooling, treating with 50 ml. of 10% potassium bisulfate and stirring until two clear layers are obtained. After separating, the aqueous phase is extracted with ethyl acetate (3×50 ml.), the combined organic layers are dried (MgSO$_4$), and the solvent evaporated to give 2.8 g. (55%) of trans-1[D-(3-acetylthio)-2-methyl-1-oxopropyl]-4-[[(methylamino)carbonyl]oxy]-L-proline as a foamy hygroscopic residue.

EXAMPLE 2 trans-1-(D-3-Mercapto-2-methyl-1-oxopropyl)-4-[[(methylamino)carbonyl]oxy]-L-proline Argon is passed through a cold solution of 6 ml. of concentrated ammonium hydroxide in 4 ml. of water for 10 minutes. The latter is then added while cooling and under a blanket of argon to the product of Example 1 and the mixture is swirled in an icebath until a pale yellow solution is obtained (about 3 minutes). Stirring under argon is continued at room temperature for a total of 2 hours, then the solution is extracted with 20 ml. of ethyl acetate (this and subsequent operations are carried out as much as possible under an argon atmosphere). The aqueous layer is cooled, stirred, layered over with 20 ml. of ethyl acetate and acidified portionwise with approximately 13 ml. of 1:1 hydrochloric acid. The layers are separated, the aqueous phase is extracted with additional ethyl acetate (3×20 ml.), the combined ethyl acetate layers are dried (MgSO$_4$), and the solvent evaporated to give trans-1-(D-3-mercapto-2-methyl-1-oxopropyl)-4-[[(methylamino)carbonyl]oxy]-L-proline as a sticky foamy residue. The latter is rubbed under ether and the evaporation repeated, finally at 0.1–0.2 mm., to yield 2.2 g. (90%) of the product as a colorless, somewhat hygroscopic, amorphous solid, m.p. 54°–57° (S, 45°). [α]$_D^{26}$ −53° (c, 1% in EtOH).

The racemic forms of the final products in each of the foregoing examples are produced by utilizing the DL-form of the starting amino acid instead of the L-form.

Similarly, the D-form of the final products in each of the foregoing examples is produced by utilizing the D-form of the starting amino acid instead of the L-form.

EXAMPLE 3

(a) N-Carbobenzyloxy-cis-4-hydroxy-L-proline, methyl ester 6.5 g (0.024 mole) of N-carbobenzyloxy-cis-4-hydroxy-L-proline [J.A.C.S., 79, 189 (1957)] is dissolved in 65 ml. of methanol, stirred, and treated with 0.65 ml. of concentrated sulfuric acid. After stirring at room temperature for one-half hour, the solution is allowed to stand overnight. The bulk of solvent is removed on a rotary evaporator and the oily residue (13 g.) is taken up in 70 ml. of ether and washed with 35 ml. of 10% sodium bicarbonate solution. The wash is back extracted with 35 ml. of ether. The combined organic layers are dried (MgSO$_4$), and the ether is evaporated to give 6.5 g. (96%) of product as a pale yellow viscous oil. [α]$_D^{25}$ −24° (c, 1% in chloroform).

(b) cis-N-Carbobenzyloxy-4-[[(methylamino)carbonyl]oxy]-L-proline, methyl ester

To a stirred solution of 5.4 g. (0.019 mole) of N-carbobenzyloxy-cis-4-hydroxy-L-proline, methyl ester, in 120 ml. of acetonitrile is added 5.4 ml. of triethylamine, followed by 5.4 ml. of methyl isocyanate. After keeping overnight at room temperature and refluxing for two hours, the reaction mixture is worked up as in Example 1c to give 5.6 g (86%) of a pale yellow viscous oil.

(c) cis-N-Carbobenzyloxy-4-[[(methylamino)carbonyl]oxy]-L-proline

The crude ester from part b (5.6 g; 0.017 mole) is saponified with 11 ml. (0.022 mole) of 2 N sodium hydroxide in 45 ml. of methanol as in Example 1d to give 5.1 g of a foamy residue. The colorless cyclohexylamine salt, prepared in 25 ml. of ethanol and 400 ml. of ether employing 1.7 g. of cyclohexylamine, weighs 4.8 g.; m.p. 171°–173°. [α]$_D^{25}$ −16° (c, 1% in ethanol). A sample recrystallized from ethanol-ether shows no change in melting point or optical rotation.

The cyclohexylamine salt yields 3.5 g. (65%) of the free acid as a colorless foamy residue.

(d) cis-4-[[(Methylamino)carbonyl]oxy]-L-proline 3.5 g (0.011 mole) of cis-N-carbobenzyloxy-4-[[(methylamino)carbonyl]oxy]-L-proline is hydrogenated in 130 ml. of 2:1 methanol-water employing 1.3 g of 2:1 methanol-water employing 1.3 g. of 5% palladium-carbon as in Example 1e to give 1.9 g. (95%) of product as a greyish solid; m.p. 232°-234° (dec.), preceded by gradual darkening and sintering. $[\alpha]_D^{25}$ —42° (c, 0.5% in 1:1 methanol-water).

(e)
cis-1-[D-(3-Acetylthio)-2-methyl-1-oxopropyl]-4-[[(methylamino)carbonyl]oxy]-L-proline Interaction of 1.85 g (0.0098 mole) of cis-4-[[(methylamino)carbonyl]oxy]-L-proline and 2.0 g (0.011 mole) of D-3-acetylthio-2-methylpropanoyl chloride in 30 ml. of water in the presence of sodium carbonate as in Example 1f yields 3.35 g. of a gummy product. The dicyclohexylamino salt, prepared in 35 ml. of ethyl acetate employing 1.8 g. of dicyclohexylamine, weighs 4.0 g.; m.p. 177°-179°. $[\alpha]_D^{25}$ —54° (c, 1% in methanol). Following trituration with 20 ml. of acetonitrile and cooling, the colorless solid weighs 3.6 g.; m.p. 179°-181°. $[\alpha]_D^{25}$ —54° (c, 1% in methanol). Treatment with 10% potassium bisulfate and extraction into ethyl acetate yields 2.5 g. (76%) of the free acid as a colorless foamy residue.

EXAMPLE 4 cis-1-(D-3-Mercapto-2-methyl-1-oxopropyl)-4-[[(methylamino)carbonyl]oxy]-L-proline By treating the material of Example 3 with 5.5 ml. of concentrated ammonium hydroxide in 12.5 ml. of water according to the procedure described in Example 2, 1.8 g. (82%) of the product is obtained as a colorless, hygroscopic, sticky foam. $[\alpha]_D^{25}$ —59° (c, 1% in ethanol).

EXAMPLE 5 cis-1-[D-(3-Acetylthio)-2-methyl-1-oxopropyl]-4-[[(ethylamino)carbonyl]oxy]-L-proline Utilizing the procedure of Example 3 but substituting ethylisocyanate for the methylisocyanate in part b, cis-1-[D-(3-acetylthio)-2-methyl-1-oxopropyl]-4-[[(ethylamino)carbonyl]oxy]-L-proline is obtained.

EXAMPLE 6 cis-1-(D-3-Mercapto-2-methyl-1-oxopropyl)-4-[[(ethylamino)carbonyl]oxy]-L-proline By treating the material of Example 5 with ammonia according to the procedure described in Example 4, cis-1-(D-3-mercapto-2-methyl-1-oxopropyl)-4-[[(ethylamino)carbonyl]oxy]-L-proline is obtained.

EXAMPLE 7 cis-1-[D-(3-Acetylthio)-2-methyl-1-oxopropyl]-4-[[(propylamino)carbonyl]oxy]-L-proline Utilizing the procedure of Example 3 but substituting n-propylisocyanate for the methylisocyanate in part b, cis-1-[D-(3-acetylthio)-2-methyl-1-oxopropyl]-4-[[(propylamino)carbonyl]oxy]-L-proline is obtained.

EXAMPLE 8 cis-1-(D-3-Mercapto-2-methyl-1-oxopropyl)-4-[[(propylamino)carbonyl]oxy]-L-proline By treating the material of Example 7 with ammonia according to the procedure described in Example 4, cis-1-(D-3-mercapto-2-methyl-1-oxopropyl)-4-[[(propylamino)carbonyl]oxy]-L-proline is obtained.

EXAMPLE 9 cis-1-[D-(3-Acetylthio)-2-methyl-1-oxopropyl]-4-[[(phenylamino)carbonyl]oxy-]-L-proline Utilizing the procedure of Example 3 but substituting phenylisocyanate for the methylisocyanate in part b, cis-1-[D-(3-acetylthio)-2-methyl-1-oxopropyl]-4-[[(phenylamino)carbonyl]oxy]-L-proline is obtained.

EXAMPLE 10 cis-1-(D-3-Mercapto-2-methyl-1-oxopropyl)-4-[[(phenylamino)carbonyl]oxy]-L-proline By treating the material from Example 9 with ammonia according to the procedure described in Example 4, cis-1-(D-3-mercapto-2-methyl-L-oxopropyl)-4-[[(phenylamino)carbonyl]oxy]-L-proline is obtained.

EXAMPLE 11 cis-1-[D-(3-Acetylthio)-2-methyl-1-oxopropyl]-4-[[(4-chlorophenyl)carbonyl]oxy]-L-proline Utilizing the procedure of Example 3 but substituting 4-chlorophenylisocyanate for the methylisocyanate in part b, cis-1-[D-(3-acetylthio)-2-methyl-1-oxypropyl]-4-[[(4-chlorophenyl)carbonyl]oxy]-L-proline is obtained.

EXAMPLE 12 cis-1-(D-3-Mercapto-2-methyl-1-oxopropyl)-4-[[(4-chlorophenyl)carbonyl]oxy]-L-proline By treating the material from Example 11 with ammonia according to the procedure described in Example 4, cis-1-(D-3-mercapto-2-methyl-1-oxopropyl)-4-[[(4-chlorophenyl)carbonyl]oxy]-L-proline is obtained.

EXAMPLE 13 cis-1-[D-(3-Acetylthio)-2-methyl-1-oxopropyl]-4-[[(3-trifluoromethylphenyl)carbonyl]oxy]-L-proline Utilizing the procedure of Example 3 but substituting 3-trifluoromethylphenylisocyanate in place of the methylisocyanate in part b, cis-1-[D-(3-acetylthio)-2-methyl-1-oxopropyl]-4-[[(3-trifluoromethylphenyl)carbonyl]oxy]-L-proline is obtained.

EXAMPLE 14 cis-1-[D-(Acetylthio)-2-methyl-1-oxopropyl]-4-[[(2-methoxyphenyl)carbonyl]oxy]-L-proline Utilizing the procedure of Example 3 but substituting 2-methoxyphenylisocyanate for methylisocyanate in part b, cis-1-[D-(acetylthio)-2-methyl-1-oxopropyl]-4-[[(2-methoxyphenyl)carbonyl]oxy]-L-proline is obtained.

EXAMPLE 15 trans-1-[D-(Benzoylthio)-2-methyl-1-oxopropyl]-4-[[(2-ethylphenyl)carbonyl]oxy]-L-proline Utilizing the procedure of Example 1 but substituting 2-ethylphenylisocyanate for the methylisocyanate in part c and D-3-benzoylthio-2-methylpropanoyl chloride for the D-3-acetylthio-2-methylpropanoyl chloride in part f, trans-1-[D-(benzoylthio)-2-methyl-1-oxopropyl]-4-[[(2-ethylphenyl)carbonyl]oxy]-L-proline is obtained.

EXAMPLE 16 trans-1-[D-(Phenacetylthio)-2-methyl-1-oxopropyl]-4-[[(4-methylthiophenyl)carbonyl]oxy]-L-proline Utilizing the procedure of Example 1 but substituting 4-methylthiophenylisocyanate for the methylisocyanate in part c, and D-phenylacetylthio-2-methylpropanoyl chloride for the D-(3-acetylthio)-2-methylpropanoyl chloride in part f, trans-1-[D-(phenacetylthio)-2-methyl-1-oxopropyl]-4-[[(4-methylthiophenyl)carbonyl]oxy]-L-proline is obtained.

EXAMPLE 17 trans-1-[D-(3-Phenylpropionylthio)-2-methyl-1-oxopropyl]-4-[[(3-bromophenyl)carbonyl]oxy]-L-proline Utilizing the procedure of Example 1 but substituting 3-bromophenylisocyanate for the methylisocyanate in part c, and D-(3-phenylpropionylthio)-2-methylpropanoyl chloride for the D-(3-acetylthio)-2-methylpropanoyl chloride in part f, trans-1-[D-(3-phenylpropionylthio)-2-methyl-1-oxopropyl]-4-[[(3-bromophenyl)carbonyl]oxy]-L-proline is obtained.

EXAMPLE 18 trans-1-[D-(3-Acetylthio)-2-methyl-1-oxopropyl]-4-[[(cyclopentylamino)carbonyl]oxy]-L-proline Utilizing the procedure of Example 1 but substituting cyclopentylisocyanate for the methylisocyanate in part c, trans-1-[D-(3-acetylthio)-2-methyl-1-oxopropyl]-4-[[(cyclopentylamino)carbonyl]oxy]-L-proline is obtained.

EXAMPLE 19 trans-1-[D-(3-Acetylthio)-2-methyl-1-oxopropyl]-4-[[(cyclohexylamino)carbonyl]oxy]-L-proline Utilizing the procedure of Example 1 but substituting cyclohexylisocyanate for the methylisocyanate in part c, trans-1-[D-(3-acetylthio)-2-methyl-1-oxopropyl]-4-[[(cyclohexylamino)carbonyl]oxy]-L-proline is obtained.

EXAMPLE 20 cis-1-[D-(3-Acetylthio)-2-methyl-1-oxopropyl]-4-[[(allylamino)carbonyl]oxy]-L-proline Utilizing the procedure of Example 3 but substituting allylisocyanate for the methylisocyanate in part b, cis-1-[D-(3-acetylthio)-2-methyl-1-oxopropyl]-4-[[(allylamino)carbonyl]oxy]-L-proline is obtained.

EXAMPLE 21 cis-1-(D-3-Mercapto-2-methyl-1-oxopropyl)-4-[[(allylamino)carbonyl]oxy]-L-proline By treating the material from Example 20 with ammonia according to the procedure described in Example 4, cis-1-(D-3-mercapto-2-methyl-1-oxopropyl)-4-[[(allylamino)carbonyl]oxy]-L-proline is obtained.

EXAMPLE 22 trans-1-[D-(3-Acetylthio)-2-methyl-1-oxopropyl]-4-[[(dimethylamino)carbonyl]oxy]-L-proline (a) trans-N-Carbobenzyloxy-4-[[(dimethylamino)carbonyl]oxy]-L-proline, methyl ester A solution of N-carbobenzyloxy-trans-4-hydroxy-L-proline methyl ester (Example 1, part b) in chloroform is treated dropwise with an equivalent quantity of dimethylcarbamyl chloride. The mixture is stirred for two hours, washed with water and the organic phase is dried over MgSO$_4$. The solution is filtered and solvent evaporated to give trans-N-carbobenzyloxy-4-[[(dimethylamino)carbonyl]oxy]-L-proline, methyl ester.

(b) trans-N-Carbobenzyloxy-4-[[(dimethylamino)carbonyl]oxy]-L-proline

Hydrolysis of the methyl ester from part a with sodium hydroxide solution in the manner described in Example 1, part d, gives trans-N-carbobenzyloxy-4-[[(dimethylamino)carbonyl]oxy]-L-proline.

(c) trans-4-[[(Dimethylamino)carbonyl]oxy]-L-proline

Hydrogenation of the material from part b according to the procedure described in Example 1, part e, gives trans-4-[[(dimethylamino)carbonyl]oxy]-L-proline.

(d) trans-1-[D-(3-Acetylthio)-2-methyl-1-oxopropyl]-4-[[(dimethylamino)carbonyl]oxy]-L-proline Treatment of the material from part c with an equivalent quantity of D-3-acetylthio-2-methylpropanoyl chloride according to the procedure described in Example 1, part f, gives trans-1-[D-(3-acetylthio)-2-methyl-1-oxopropyl]-4-[[(dimethylamino)carbonyl]oxy]-L-proline.

EXAMPLE 23 trans-1-[D-(3-Acetylthio)-2-methyl-1-oxopropyl]-4-[[(pyrrolidino)carbonyl]oxy]-L-proline Utilizing the procedure described in the preparation of Example 22 but substituting pyrrolidinocarbamyl chloride for the dimethylaminocarbamyl chloride in part a, trans-1-[D-(3-acetylthio)-2-methyl-1-oxopropyl]-4-[[(pyrrolidino)carbonyl]oxy]-L-proline is obtained.

EXAMPLE 24 trans-1-[D-(3-Acetylthio)-2-methyl-1-oxopropyl]-4-[[(piperidino)carbonyl]oxy]-L-proline Utilizing the procedure described in the preparation of Example 22, but substituting piperidinocarbamyl chloride for the dimethylaminocarbamyl chloride in part a, trans-1-[D-(3-acetylthio)-2-methyl-1-oxopropyl]-4-[[(piperidino)carbonyl]oxy]-L-proline is obtained.

EXAMPLE 25 trans-1-[D-(3-Acetylthio)-2-methyl-1-oxopropyl]-4-[[(morpholino)carbonyl]oxy]-L-proline Utilizing the procedure used in the preparation of Example 22 but substituting morpholinocarbamyl chloride for the dimethylaminocarbamyl chloride in part a, trans-1-[D-(3-acetylthio)-2-methyl-1-oxopropyl]-4-[[(morpholino)carbonyl]oxy]-L-proline is obtained.

EXAMPLE 26 trans-1-(2-Acetylthio-1-oxoethyl)-4-[[(methylamino)carbonyl]oxy]-L-proline

Utilizing the procedure described in the preparation of Example 1 but substituting 2-acetylthioacetyl chloride for the D-(3-acetylthio)-2-methylpropanoyl chloride in part f, trans-1-(2-acetylthio-1-oxoethyl)-4-[[(methylamino)carbonyl]oxy]-L-proline is obtained.

EXAMPLE 27 trans-1-(4-Acetylthio-1-oxobutyl)-4-[[(methylamino)carbonyl]oxy]-D-proline

Utilizing the procedure described in the preparation of Example 1 but substituting trans-4-hydroxy-D-proline for the trans-4-hydroxy-L-proline in part a, and 4-acetylthiobutyroyl chloride for the D-(3-acetylthio)-2-methylpropanoyl chloride in part f, trans-1-(4-acetylthio-1-oxobutyl)-4-[[(methylamino)carbonyl]oxy]-D-proline is obtained.

EXAMPLE 28 cis-1-(4-Acetylthio-4-methyl-1-oxobutyl)-3-[[(methylamino)carbonyl]oxy]-L-proline Utilizing the procedure described in the preparation of Example 3 but substituting 4-acetylthiovaleroyl chloride for the D-3-(acetylthio)-3-methylpropionyl chloride in part e, cis-1-(4-acetylthio-4-methyl-1-oxobutyl)-3-[[(methylamino)carbonyl]oxy]-L-proline is obtained.

EXAMPLE 29 trans-1-[L-(3-Acetylthio)-2-ethyl-1-oxopropyl]-3-[[(methylamino)carbonyl]oxy]-L-proline Utilizing the procedure of Example 1 but substituting trans-3-hydroxy-L-proline for trans-4-hydroxy-L-proline in part a and L-(3-acetylthio)-2-ethylpropionyl chloride for the D-3-(acetylthio)-3-methylpropionyl chloride in part f, trans-1-[L-(3-acetylthio)-2-ethyl-1-oxopropyl]-3-[[(methylamino)carbonyl]oxy]-L-proline is obtained.

EXAMPLE 30 trans-1-[D-(3-Acetylthio)-2-methyl-1-oxopropyl]-4-[(aminocarbonyl)oxy]-L-proline (a)
trans-N-Carbobenzyloxy-4-[(aminocarbonyl)oxy]-L-proline, methyl ester A solution of equivalent quantities of N-carbobenzyloxy-trans-4-hydroxy-L-proline, methyl ester from Example 1, part b, and dimethylaniline is treated with a solution of phosgene in toluene. After standing overnight an equivalent quantity of ammonia is passed through the solution of trans-N-carbobenzyloxy-4-[(chlorocarbonyl)oxy]-L-proline, methyl ester. After standing for twelve hours at room temperature, the solution is washed with water, dried over magnesium sulfate, filtered and the solvent evaporated to give trans-N-carbobenzyloxy-4-[(aminocarbonyl)oxy]-L-proline, methyl ester.

(b)
trans-N-Carbobenzyloxy-4-[(aminocarbonyl)oxy]-L-proline

Hydrolysis of the methyl ester from part a with sodium hydroxide solution in the manner described in Example 1, part d, gives trans-N-carbobenzyloxy-4-[(aminocarbonyl)oxy]-L-proline.

(c) trans-4-[(Aminocarbonyl)oxy]-L-proline

Hydrogenation of the material from part b according to the procedure described in Example 1, part e, gives trans-4-[(aminocarbonyl)oxy]-L-proline.

(d)
trans-1-[D-(3-Acetylthio)-2-methyl-1-oxopropyl]-4-[(aminocarbonyl)oxy]-L-proline Treatment of the material from part c with an equivalent quantity of D-3-acetylthio-2-methylpropanoyl chloride according to the procedure described in Example 1, part f, gives trans-1-[D-(3-acetylthio)-2-methyl-1-oxopropyl]-4-[(aminocarbonyl)oxy]-L-proline.

EXAMPLE 31 trans-1-[D-(3-Acetylthio)-2-methyl-1-oxopropyl]-4-[[(diisopropylamino)carbonyl]oxy]-L-proline Utilizing the procedure of Example 30, but substituting diisopropylamine for the ammonia in part a, trans-1-[D-[3-acetylthio)-2-methyl-1-oxopropyl]-4-[[(diisopropylamino)carbonyl]oxy]-L-proline is obtained.

EXAMPLE 32 trans-1-[D-(3-Acetylthio)-2-methyl-1-oxopropyl]-4-[[(cyclopropylamino)carbonyl]oxy]-L-proline Utilizing the procedure of Example 30, but substituting cyclopropylamine for the ammonia in part a, trans-1-[D-(3-acetylthio)-2-methyl-1-oxopropyl]-4-[[(cyclopropylamino)carbonyl]oxy]-L-proline is obtained.

EXAMPLE 33 trans-1-[D-(3-Acetylthio)-2-methyl-1-oxopropyl]-4-[[(n-butylamino)carbonyl]oxy]-L-proline Utilizing the procedure of Example 30, but substituting n-butylamine for the ammonia in part a, trans-1-[D-(3-acetylthio)-2-methyl-1-oxopropyl]-4-[[(n-butylamino)carbonyl]oxy]-L-proline is obtained.

EXAMPLE 34 trans-1-[D-(3-Acetylthio)-2-methyl-1-oxopropyl]-4-[[(propargylamino)carbonyl]oxy]-L-proline Utilizing the procedure of Example 30, but substituting propargylamine for the ammonia in part a, trans-1-[D-(3-acetylthio)-2-methyl-1-oxopropyl]-4-[[(propargylamino)carbonyl]oxy]-L-proline is obtained.

EXAMPLE 35 trans-1-[D-(3-Acetylthio)-2-methyl-1-oxopropyl]-4-[[(methylamino)carbonyl]oxy]-L-proline, methyl ester A solution of the material from Example 1 in ether is treated with a slight excess of diazomethane. After stirring at room temperature for two hours, the solvent is evaporated to give trans-1-[D-(3-acetylthio)-2-methyl-1-oxopropyl]-4-[[(methylamino)carbonyl]oxy]-L-proline, methyl ester.

EXAMPLE 36

S,S-Dimer of trans-1-(D-3-mercapto-2-methyl-1-oxopropyl)-4-[[(methylamino)carbonyl]oxy]-L-proline A solution of the material from Example 2 is dissolved in ethanol, stirred and treated with a solution of one equivalent of iodine in ethanol. The pH of the solution is maintained at 6-7 by the addition of N sodium hydroxide solution. The solvent is evaporated and the residue is extracted with ethyl acetate. After drying over MgSO$_4$, the solution is filtered and the solvent is removed to give S,S-dimer of trans-1-(D-3-mercapto-2-methyl-1-oxopropyl)-4-[[(methylamino)carbonyl]oxy]-L-proline.

EXAMPLE 37

S,S-Dimer of cis-1-(D-3-mercapto-2-methyl-1-oxopropyl)-4-[[(methylamino)carbonyl]oxo]-L-proline Oxidation of the material from Example 4 with a solution of iodine according to the procedure used in Example 36 gives S,S-dimer of cis-1-(D-3-mercapto-2-methyl-1-oxopropyl)-4-[[(methylamino)carbonyl]oxo]-L-proline.

EXAMPLE 38

Sodium salt of trans-1-[D-(3-acetylthio)-2-methyl-1-oxopropyl]-4-[[(methylamino)carbonyl]oxy]-L-proline A solution of 2.9 g of material from Example 1 in 25 ml of water is treated with 0.84 g of sodium bicarbonate. The solution is freeze-dried to give the sodium salt of trans-1-[D-(3-acetylthio)-2-methyl-1-oxopropyl]-4-[[(methylamino)carbonyl]oxy]-L-proline.

EXAMPLE 39

1000 tablets each containing 100 mg. of active substance are produced from the following ingredients:

| | |
|---|---|
| cis-1-(D-mercapto-2-methyl-1-oxopropyl)-4-[[(methylamino)carbonyl]oxy]-L-proline | 100 g. |
| Corn starch | 50 g. |
| Gelatin | 7.5 g. |
| Avicel (microcrystalline cellulose) | 25 g. |
| Magnesium stearate | 2.5 g. |

The cis-1-(D-3-mercapto-2-methyl-1-oxopropyl)-4-[[(methylamino)carbonyl]oxy]-L-proline and corn starch are admixed with an aqueous solution of the gelatin. The mixture is dried and ground to a fine powder. The Avicel and then the magnesium stearate are admixed with the granulation. This is then compressed in a tablet press to form 1000 tablets each containing 100 mg. of active ingredient.

EXAMPLE 40

1000 tablets each containing 200 mg. of trans-1-(D-3-mercapto-1-oxopropyl)-4-[[(methylamino)carbonyl]oxy]-L-proline are produced from the following ingredients:

| | |
|---|---|
| trans-1-(D-3-mercapto-1-oxopropyl)-4-[[(methylamino)carbonyl]oxy]-L-proline | 200 g. |
| Lactose | 100 g. |
| Avicel | 150 g. |
| Corn Starch | 50 g. |
| Magnesium stearate | 5 g. |

The trans-1-(D-3-mercapto-1-oxopropyl)-4-[[(methylamino)carbonyl]oxy]-L-proline, lactose and Avicel are admixed, then blended with the corn starch. Magnesium stearate is added. The dry mixture is compressed in a tablet press to form 1000 505 mg. tablets each containing 200 mg. of active ingredient. The tablets are coated with a solution of Methocel E 15 (methyl cellulose) including as a color a lake containing yellow #6.

EXAMPLE 41

Two piece #1 gelatin capsules each containing 250 mg. of trans-1-(D-3-mercapto-2-methyl-1-oxopropyl)-4-[[(methylamino)carbonyl]oxy]-L-proline are filled with a mixture of the following ingredients:

| | |
|---|---|
| trans-1-(D-3-mercapto-2-methyl-1-oxopropyl)-4-[[(methylamino)carbonly]oxy]-L-proline | 125 mg. |
| Magnesium stearate | 3 mg. |
| USP lactose | 100 mg. |

EXAMPLE 42

An injectable solution is produced as follows:

| | |
|---|---|
| trans-1-(D-3-mercapto-2-methyl-1-oxopropyl-4-[[(methylamino)carbonyl]oxy]-L-proline | 500 g. |
| Methyl paraben | 5 g. |
| Propyl paraben | 1 g. |
| Sodium chloride | 25 g. |
| Water for injection qs. | 5 l. |

The active substance, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains 5 ml. of solution in a concentration of 100 mg. of active ingredient per ml. of solution for injection.

What is claimed is:

1. A compound of the formula

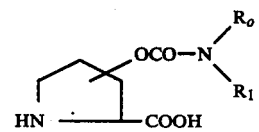

wherein $R_o$ and $R_1$ each is hydrogen, lower alkyl, allyl, propargyl, cyclo-lower alkyl, phenyl or phenyl substituted with a halogen, lower alkyl, lower alkoxy, lower alkylthio or trifluoromethyl group, or $R_o$ and $R_1$ complete a pyrrolidine, piperidine or morpholine ring.

2. A compound as in claim 1 wherein $R_o$ is lower alkyl.

3. A compound as in claim 1 wherein $R_o$ is methyl and $R_1$ is hydrogen.

* * * * *